United States Patent [19]

Strul et al.

[11] Patent Number: 4,807,620

[45] Date of Patent: Feb. 28, 1989

[54] APPARATUS FOR THERMAL ANGIOPLASTY

[75] Inventors: Bruno Strul, Palo Alto; Tsvi Goldenberg, Irvine, both of Calif.

[73] Assignee: Advanced Interventional Systems, Inc., Irvine, Calif.

[21] Appl. No.: 53,391

[22] Filed: May 22, 1987

[51] Int. Cl.⁴ .............................................. A61B 17/39
[52] U.S. Cl. .................................... 128/303.1; 128/401
[58] Field of Search ...................... 128/303.1, 401, 804; 219/10.79, 10.41, 233

[56] References Cited

U.S. PATENT DOCUMENTS

| | | | |
|---|---|---|---|
| 3,934,115 | 1/1976 | Peterson | 219/223 |
| 4,154,246 | 5/1979 | LeVeen | 128/804 |
| 4,256,945 | 3/1981 | Carter et al. | 219/10.75 |
| 4,446,874 | 5/1984 | Vaguine | 128/804 |
| 4,534,347 | 8/1985 | Taylor | 128/303.1 |
| 4,582,057 | 4/1986 | Auth et al. | 128/303.1 |
| 4,643,186 | 2/1987 | Rosen et al. | 128/303.1 |
| 4,654,024 | 3/1987 | Crittenden et al. | 128/303.1 |
| 4,701,587 | 10/1987 | Carter et al. | 219/233 X |

FOREIGN PATENT DOCUMENTS 1284528 12/1968 Fed. Rep. of Germany ... 128/303.1

Primary Examiner—Lee S. Cohen
Attorney, Agent, or Firm—Jackson & Jones

[57] ABSTRACT

An interventional therapeutic apparatus is described which includes a probe in the form of a transmission line such as coaxial cable. The probe is adapted to pass through the interior of a body cavity such as a blood vessel and includes an inductive load such as a ferrite bead at the remote end of the cable. Radio frequency energy is applied to the cable and converted into heat by a ferrite bead. As a result of the heat conversion by the ferrite bead, the remote end of the coaxial cable is heated to a sufficient temperature to provide the effect desired, for example to melt or otherwise remove plaque deposits in blood vessels.

25 Claims, 2 Drawing Sheets

APPARATUS FOR THERMAL ANGIOPLASTY

BACKGROUND OF THE INVENTION

1. Field of the Invention

This present invention relates to an apparatus and method for applying heat to tissue within a body cavity for therapeutic purposes.

2. Description of the Prior Art

As a natural consequence of aging and other biochemical factors, atherosclerotic obstructions consisting of fatty deposits, fibrous tissue and eventually calcium, tend to form on the vessel walls of the human coronary, peripheral and cerebral vasculature. As this accumulation progresses, the lumen of the artery is narrowed (or, sometimes completely blocked), restricting or preventing adequate supply of oxygenated blood to supply the muscles of the heart or legs.

The state of inadequate oxygenation, known as "ischemia," when it occurs in the coronary arteries, results in abnormalities of the biochemical, electrical and mechanical functions of the heart. The clinical manifestation of this condition may include angina pectoris, acute myocardial infarction or ventricular arrhythmia that can lead to sudden death.

In the peripheral arteries, the ischemia condition commonly occurs with exercise and is termed "intermittent claudication," i.e., the pain that occurs in a muscle with inadequate blood supply that is stressed by exercise. Pain may also occur at rest and may be continuous in the toes and foot. Occasionally numbness or paresthesias may be present. Ulceration and gangrene of the toes and distal foot are common when the disease reaches advanced stages. Amputation is sometimes required.

Many therapeutic interventions have been available to treat coronary, peripheral and cerebral vascular disease. Drugs that dilate the vessel and lower blood viscosity are prescribed to prevent or lessen an ischemic attack.

The introduction of polyvinyl balloon tipped catheters marked the beginning of a new era in revascularization techniques. These catheters are threaded through the vasculature, via a percutaneous incision, to the site of occlusion. The balloon is then inflated using an accessory device located outside the body. As the balloon inflates, the lumen of the artery is increased to allow for greater blood flow resulting in the alleviation of symptoms.

Bypass surgery is frequently prescribed. Grafting a healthy vessel around the diseased one provides a new connection for blood flow to the portion of the artery that is distal to the diseased section.

More recent treatment techniques have focused on the use of high energy laser light pulses conducted through a fiber optic bundle to remove atherosclerotic deposits.

The use of laser energy has also been used to heat a metal tipped catheter which then melts or dissolves the plaque. Lasers, however, are complex, relatively large, expensive and very inefficient. The use of lasers for removing plaque deposits is still in the formative stages.

In addition to the use of expandable balloons and lasers, it has been suggested in U.S. Pat. No. 4,643,186 that the plaque deposits be radiated with microwave energy via a transmission line inserted through the affected artery. Such a technique has several inherent problems. For example, the plaque will provide a variable load to the microwave source depending upon the moisture content of the plaque. Such a variable load makes it difficult to control the amount of power applied to the plaque to vaporize or otherwise remove the same without creating a risk of damaging the vessel wall.

There is a need for a simple and effective apparatus for reducing the occlusive effect of plaque deposits within blood vessels.

SUMMARY OF THE INVENTION

In accordance with the present invention, an interventional therapeutic apparatus is provided for the remote delivery of heat to body tissue. The apparatus may be employed, for example, to reduce the occlusive effect of plaque deposits in blood vessels. The apparatus includes a probe in the form of a transmission line such as a coaxial cable having proximal and distal ends. The transmission line probe is adapted to pass through the interior of a body cavity such as a blood vessel. An inductive load such as a ferrite bead or core is disposed at the distal end of the transmission line, the load being arranged to convert radio frequency (r.f.) signals transmitted through the line into heat, with the conversion being optimal at a predetermined frequency. A variable frequency oscillator is connected to the proximal end of the transmission line for applying r.f. energy at a suitable frequency, e.g., 10 MHz to 3 GHz, to frequency of the r.f. energy is adjusted to substantially the predetermined frequency so that the inductive load is heated to a temperature sufficient to deliver the desired heat to the body tissue undergoing treatment. For example, the distal end of the line may be heated sufficiently to melt or otherwise remove plaque with which the distal end comes into contact. This enables the transmission line to be pushed through restrictive plaque deposits and reduce the occlusive effect thereof.

The magnitude of the power applied to the proximal end of the line (i.e., incident power) and the magnitude of the power reflected back from the distal end of the line (i.e., reflected power) may be measured to enable an operator to adjust the level of power delivered to the load and thereby control the temperature at the distal end of the transmission line or probe. If desired signals representative of the incident and applied power may be utilized in a closed loop system to maintain the incident power at a preset level (and thus the distal end of the line at a given temperature) and the reflected power at a minimum.

The features of the present inventions can best be understood by reference to the following descriptions taken in conjunction with the accompanying drawings, wherein like numerals indicate like components.

DESCRIPTION OF THE PREFERRED EMBODIMENT

Figure 1:
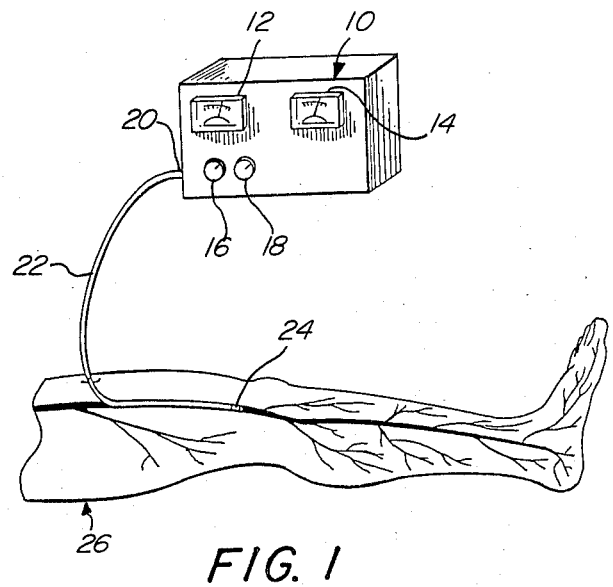
FIG. 1 is a perspective view of an apparatus of the present invention showing the probe thereof inserted into an artery in the leg of a patient.

Referring now to the drawings, and more particularly to FIG. 1, there is illustrated a housing 10 containing an oscillator or r.f. power supply, and meters 12 and 14 for providing visual indications of certain parameters, i.e., incident and reflected power as will be explained. Knob 16 allows manual control of the magnitude of the r.f. power applied to the distal end 20 of a coaxial transmission line or probe 22, and knob 18 allows manual control of the frequency of the r.f. signal or energy applied to the line. The distal end 24 of the probe, or line 22, is illustrated as being inserted into an artery in a patient's leg 26.

Figure 2:
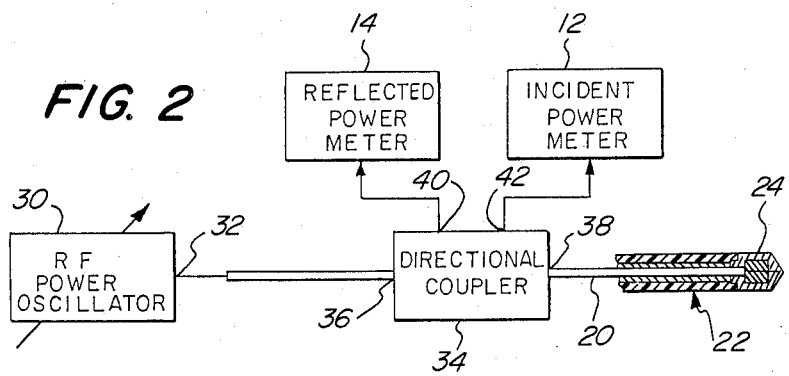
FIG. 2 is a block diagram of an electronic circuit and a diagrammatic view of a section of a probe in accordance with one embodiment of the invention.

Referring now to FIG. 2, an r.f. power supply, or oscillator unit 30, provides an r.f. signal at its output 32 which is connected to the proximal end 20 of the coaxial line 22. An r.f. power supply marketed under the Model No. M445 by Eaton Corp. with M187 Plug-In Unit may be employed as unit 30. The output power and r.f. frequency of the oscillator may be controlled by manually operated potentiometers or the like (via knobs 16 and 18), as is well known in the art, and such controls are incorporated in the unit identified above. The frequency of the r.f. energy is greater than 1 megahertz (MHz). The frequency of the r.f. energy is preferably within the range of 10 MHz to 3 gigahertz (GHz) and a most preferred range is from 500 MHz to 1.2 GHz.

A directional coupler 34 is inserted between the oscillator 30 and the proximal end 20 of the transmission line 20. The coupler 34 includes a power input 36 connected to the output 32 of the oscillator and power output 38 connected to the proximal end of the transmission line. The coupler 34 includes two signal outputs 40 & 42 which are connected to the reflected power meter 14 and the incident power meter 12, respectively. The signal on output 42 is an analog signal representing the magnitude of the power applied to the proximal end of the transmission line by the oscillator (i.e., incident power) and the signal on output 40 is an analog signal representing the magnitude of the power reflected back to the coupler 34 from the distal end 24 of the line 22 (i.e., reflected power). Meters 12 and 14, which may be of the D'Arsonval type, display the level of incident and reflected power. The coupler 34 may be of the type marketed by the Bird Electronics Corp. under the name Power Sensor and Model No. 4162W.

Figure 3:
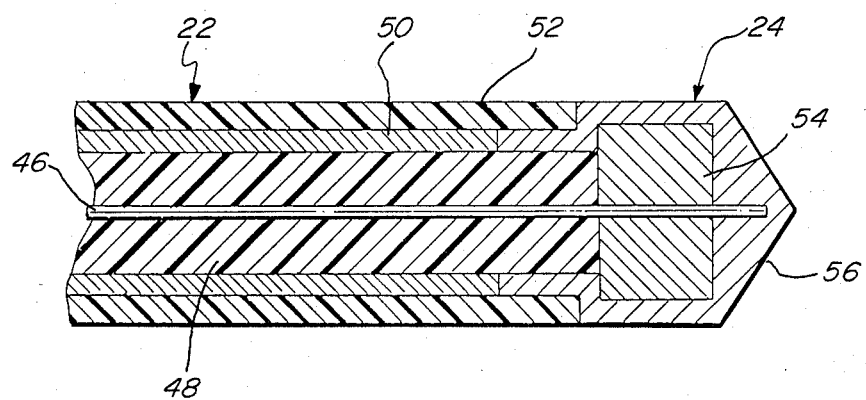
FIG. 3 is an enlarged cross-sectional view of the distal end of the probe of FIG. 2.

Referring now to FIG. 3, there is illustrated a cross-sectional view of the distal end of the transmission line 22. The line is in the form of a flexible coaxial cable having a center conductor 46, an annular insulating layer 48, an outer conducting shield 50, which may be in the form of a wire mesh, and an insulating covering material 52. An inductive load such as a ferrite bead or core 54 is disposed at the distal end of the line between the central conductor 46 and the outer conducting shield 50, as shown. A cap 56 made of a suitable metal such as stainless steel, a platinum, silver or gold alloy closes the distal end 24 of the line or probe 22. The cap 56 closes the transmission line circuit at the distal end 24 by electrically connecting the center conductor and the metal sheath 50. The cap 56 is also placed in good heat-conducting relationship with the ferrite bead 54 to transfer heat therefrom to the plaque to be melted.

The inductive load or ferrite bead 54 acts as a lossy inductor load to r.f. energy transmitted down the line 22 by converting the r.f. energy to heat.

The diameter of the coaxial line or probe 22 must be small enough to be inserted into the blood vessels of interest. Preferably the diameter of the probe is within the range of 1 to 2 millimeters.

In operation, the distal end of the probe or line 22 is inserted into an artery (in which stenotic plaque is to be removed or reduced) and guided through the artery by conventional fluoroscopy techniques until the distal end of the probe abuts the plaque deposit. The frequency of the oscillator 30 is then manually tuned, e.g., by knob 18, until the reflected power is approximately at a minimum. At this frequency (and there may be more than one such frequency) the load is matched to the oscillator and line and essentially all of the power applied to the line is converted into heat within the ferrite bead or inductive load. The temperature of the probe tip (distal end 24) may then be controlled by adjusting the magnitude of the incident power (e.g., via knob 16).

The reflected power measurement at meter 14 provides an indication of the temperature of the probe tip since ferrite changes its magnetic properties as a function of temperature. When the Curie point is reached, the ferrite loses its magnetic properties and ceases to act as an inductive load, thereby limiting the maximum temperatures achievable at the probe tip.

The Curie temperature of the ferrite depends upon the alloy used. For example, a nickel-zinc ferrite alloy marketed as ferrite No. 61 by Fair-Rite Corp. of New York reaches its Curie point at about 350° C.

Figure 4:
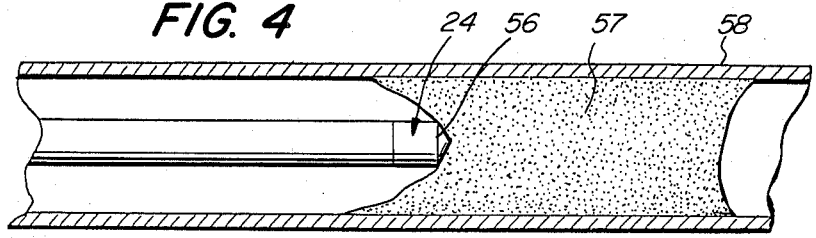
FIG. 4 illustrates the distal end of the probe of FIG. 2 inserted into an artery and abutting a plaque formation which totally occludes the artery.
Figure 5:
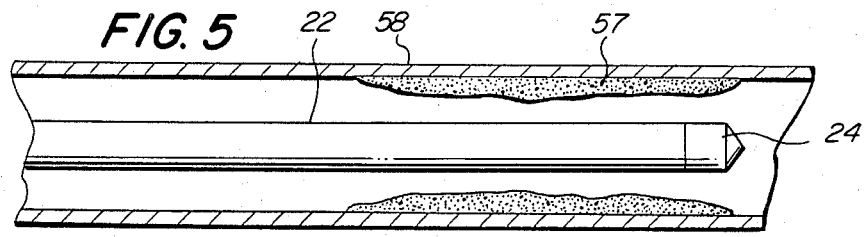
FIG. 5 illustrates how the insertion of the distal end of the probe through the plaque deposit opens a passage and reduces the occlusive effect of the plaque.

Referring now to FIGS. 4 and 5, the manner in which the probe 22 may be used to reduce the occlusive effect of atherosclerotic plaque is illustrated. The distal end 24 of the probe 22 (closed by the cap 56) when heated to a sufficient temperature melts the plaque 57 which it comes in contact with and causes a reshaping of the plaque so that a relatively smooth and open passage through the artery wall 58 is provided as illustrated in FIG. 5.

Figure 6:
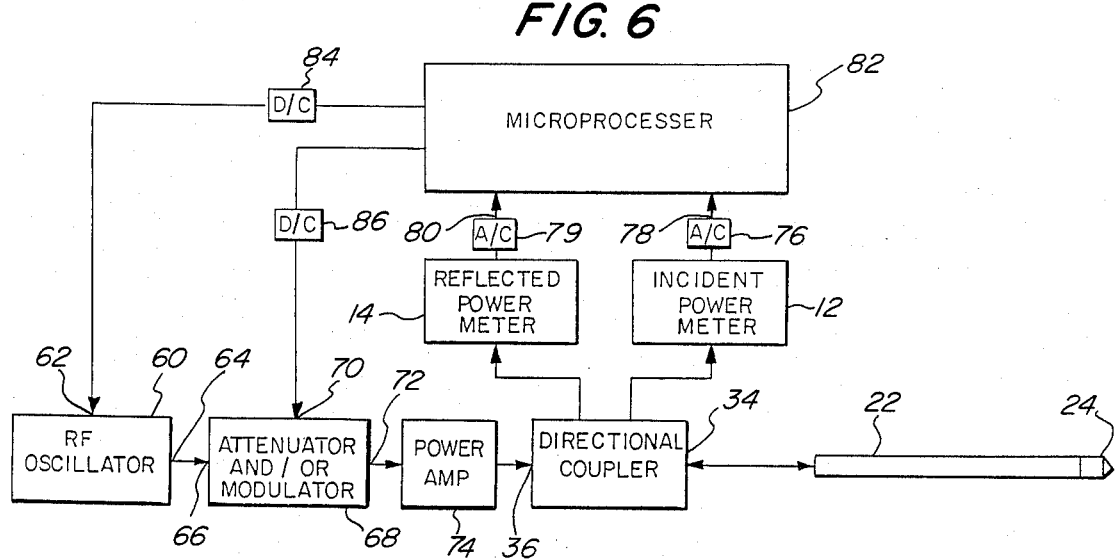
FIG. 6 is a block diagram of an alternative electronic circuit for use in the invention.

Another embodiment of the invention is illustrated in FIG. 6 in which the incident and reflected power signals are used in a closed loop to maintain the magnitude of the reflected power at a minimum and the magnitude of the incident power at a preset level. The system of FIG. 6 includes a voltage controlled oscillator 60 which has a voltage control input 62 and an r.f. output 64. The r.f. output 64 is connected to an input 66 of an attenuator or modulator 68. The attenuator 68 has a voltage control input 70 and an output 72 connected to the r.f. input 36 of the directional coupler 34 via a power amplifier 74. The incident and reflected power signals are applied via analog to digital converters 76 and 79 to input ports 78 and 80 of a microprocessor 82. The microprocessor 82 processes the incident and reflected power signals and applies output signals to the control inputs 62 and 70 of the VCO 60 and the attenuator 68 via digital to analog converters 84 and 86, as shown. The microprocessor is arranged (by appropriate programing) to change the amplitude or voltage level of signal applied to the input 62 of the VCO and thereby changing the frequency of the r.f. output at 64 as needed to minimize the level or magnitude of the reflected power signal at input port 80. The microprocessor is also arranged (by appropriate programing) to adjust the level of the signal applied to control input 72 of the attenuator 68 so that the incident power will be maintained at a level preset into the microprocessor in a well-known manner. The attenuator/modulator may be arranged to either attenuate or modulate the applied r.f. signal (from the oscillator) to thereby change the magnitude of the incident power as is well known in the art.

Figure 7:
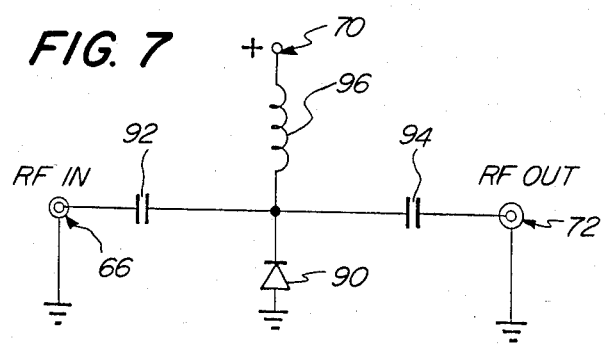
FIG. 7 is a schematic circuit diagram of an attenuator which may be used in the circuit of FIG. 6.

FIG. 7 illustrates one type of attenuator that may be employed as unit 68 in FIG. 6. The attenuator of FIG. 7 varies the amount of the attenuation of the input r.f. signal and thus the magnitude of the output signal (with a constant r.f. input at 66) by changing the amount of bias voltage on a P/N diode 90. A pair of bypass capacitors 92 and 94 are connected between the cathode of the diode and the r.f. input and output, as shown. An inductor 96 is also connected between the control input 70 and the cathode of the diode. The level of diode conduction (resulting from the level of positive bias voltage supplied by the microprocessor 82) determines how much the diode shunts the load (connected to the output 72). When the diode is reverse biased, the attenuation is effectively zero and the load is matched allowing all of the r.f. power to be transmitted to the load. As the diode turns on due to a positive bias voltage, it shunts the load and part or all of the signal is reflected back to (and absorbed by) the source or VCO 62.

In the operation of the circuit of FIG. 6, the operator merely presets the desired incident power into the microprocessor 82 and follows the procedure outlined with respect to the circuitry of FIG. 4, except that the oscillator (and attenuator) is automatically controlled.

There has thus been described a simple, efficient and reliable apparatus for the delivery of therapeutic heat to body tissue, for example to melt stenotic plaque and reduce the occlusive effect thereof in blood vessels.

The above description presents the best mode contemplated in carrying out our invention. Our invention is, however, susceptible to modifications and alternate constructions from the embodiments shown in the drawings and described above. Consequently, it is not the intention to limit the invention to the particular embodiments disclosed. On the contrary, the invention is intended and shall cover all modifications, sizes and alternate constructions falling within the spirit and scope of the invention, as expressed in the appended claims when read in light of the description and drawings.

What is claimed is:

1. In an interventional therapeutic apparatus for remote delivery of heat to body tissue, the combination which comprises:
   (a) a oscillator for providing an r.f. output signal within the range of 10 MHz to 2 GHz;
   (b) a transmission line having a proximal end connected to the oscillator for receiving the output signal and a distal end, the transmission line being constructed and arranged to pass through the interior of a body cavity; and
   (c) an inductive load dispose at the distal end of the transmission line, the inductive load comprising a magnetic material and operating to convert the r.f. signal transmitted through the transmission line into heat, the conversion being optimized at a predetermined frequency, the frequency of the output signal from the oscillator being set at substantially said predetermined frequency, whereby the inductive load is heated to a temperature sufficient for therapeutic effects.

2. The apparatus of claim 1 adapted for thermal angioplasty wherein the transmission line is constructed and arranged to pass through a blood vessel so that the occlusive effect of plaque residing within the vessel may be reduced.

3. The invention of claim 1 further including means for measuring the power reflected from the distal end of transmission line back to the proximal end of the transmission line.

4. The invention of claim 3 further including means for measuring the incident power applied to the proximal end of the transmission line by the oscillator, and means for adjusting the magnitude of the incident power.

5. The invention of claim 4 wherein the inductive load is characterized by a temperature rise up to a maximum value which is proportional to the magnitude of the difference between the incident and reflected power, whereby the temperature of the load and distal end of the transmission line can be controlled by adjusting the magnitude of the incident power while maintaining the reflected power at a predetermined level.

6. The invention of claim 5 wherein the inductive load is further characterized by a loss of ability to convert r.f. energy into heat at a preset maximum temperature.

7. The invention of claim 3 wherein the inductive load is ferrite.

8. The invention of claim 7 wherein the reflected power measuring means includes reflected power signal generating means for producing a reflected power signal representative of the magnitude of the power reflected from the distal end to the proximal end of the transmission line.

9. The invention of claim 8 wherein the oscillator further includes means for adjusting the frequency of said output signal and further including means responsive to the reflected power signal for controlling the frequency adjusting means to minimize the reflected power.

10. The invention of claim 9 further including incident power adjustment means for controlling the magnitude of the power delivered to the transmission line.

11. The invention of claim 10 further including means for providing an incident power signal representative of the magnitude of the power delivered to the transmission line by the oscillator and wherein the power adjustment means is responsive to the incident power signal for maintaining the delivered power at a present level.

12. The apparatus of claim 1 wherein the oscillator further includes means for adjusting the frequency of said output signal.

13. The invention of claim 12 further including means for measuring the power reflected from the distal end of the transmission line back to the proximal end of the transmission line, the reflected power measuring means being arranged to produce a reflected power signal and wherein the frequency adjusting means is responsive to the reflected power signal and arranged to minimize the magnitude of the reflected power.

14. A delivery system for thermal angioplasty comprising:
   (a) a coaxial transmission line having distal and proximal ends with a center conductor and an outer conducting shield and being arranged to pass through the interior of a blood vessel, the proximal end of the transmission line being adapted to be coupled to a source of r.f. energy;

(b) a core of magnetic material disposed between the center conductor and outer shield at the distal end of the transmission line, the magnetic material being arranged to convert r.f. energy into heat;

(c) a heat conductive cap closing the distal end of the transmission line and in heat conducting relationship to said core, whereby the application of r.f. energy to the proximal end of the transmission line will cause the core and cap to heat sufficiently to allow the distal end of the transmission line to be forced through plaque restricting deposits in the vessels and reduce the occlusive effect thereof.

15. The invention of claim 13 wherein the magnetic core is characterized by a temperature rise up to a predetermined maximum level which is proportional to the magnitude of the r.f. power applied to the proximal end of the transmission line with substantially minimum power being reflected back to the proximal end from the distal end of the line.

16. The delivery system of claim 15 wherein said magnetic material is ferrite.

17. The delivery system of claim 16 wherein the diameter of the distal end of the transmission line is approximately 2 mm.

18. A device for reducing the occlusive effect of plaque in blood vessels in living tissue which comprises:
(a) a coaxial transmission line having proximal and distal ends and a center conductor and outer conducting shield, the line being adapted to pass through the interior of a blood vessel;
(b) a ferrite core disposed between the center conductor and outer shield at the distal end of the transmission line;
(c) an electrically and heat conducting cap closing the distal end of the transmission line in electrical contact with the center conductor and outer shield and in heat conducting relationship with the ferrite core for providing a closed electrical circuit at the distal end of the transmission line and for receiving and dissipating heat generated in the ferrite core; and (d) power supply means coupled to the proximal end of the transmission line for applying r.f. energy thereto, whereby the r.f. energy is converted into heat by the ferrite core which heat is transmitted to the cap thereby enabling the distal end of the transmission line to ablate plaque deposits in contact with the cap and reduce the occlusive effect of such plaque within the vessel in which the transmission line is inserted.

19. The device as defined in claim 18 including means to adjust the frequency of the r.f. energy output from the power supply means to minimize the magnitude of energy reflected back to the proximal end from the distal end of the line.

20. The device as defined in claim 19 further including reflected power measuring means for measuring the magnitude of the reflected power.

21. The device as defined in claim 20 wherein the reflected power measuring means is further arranged to produce a reflected power signal representative of the magnitude of the reflected power and wherein the frequency adjusting means is responsive to the reflected power signal.

22. The device as defined in claim 21 further including means to adjust the magnitude of incident r.f. power applied to the proximal end of the transmission line and means to measure the magnitude of the incident r.f. power.

23. The device as defined in claim 22 wherein the incident power measuring means is further arranged to produce an incident power signal representative of the magnitude of the incident power and wherein the power adjustment means is responsive to the incident power signal and arranged to maintain the magnitude of the incident r.f. power at a preset level.

24. The device as defined in claim 18 wherein the power supply means is further arranged to apply r.f. energy to the transmission line within the frequency range of 1 MHz to 3 GHz.

25. The device as defined in claim 24 wherein the frequency of r.f. energy applied to the transmission line is within the range of 500 MHz to 1.2 GHz.

* * * * *